United States Patent [19]

Burk et al.

[11] 4,049,693

[45] Sept. 20, 1977

[54] 2-CHLORO-3-((4-(2,2-DICHLORO-1,1-DIFLUOROETHOXY)PHENYL)SULFONYL)-PROPANENITRILE

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 758,284

[22] Filed: Jan. 10, 1977

[51] Int. Cl.$^2$ .......................................... C07C 121/75
[52] U.S. Cl. ................................ 260/465 F; 424/304
[58] Field of Search .................................... 260/465 F

[56] References Cited

U.S. PATENT DOCUMENTS

| 3,140,226 | 7/1964 | Stephens et al. | 424/304 |
| 3,140,306 | 7/1964 | Heininger | 260/465 G |

Primary Examiner—Dolph H. Torrence
Attorney, Agent, or Firm—Theodore Post; C. Kenneth Bjork

[57] ABSTRACT

The compound 2-chloro-3-((4-(2,2-dichloro-1,1-difluoroethoxy)phenyl)sulfonyl)propanenitrile. The compound has antimicrobial utility.

1 Claim, No Drawings

2-CHLORO-3-((4-(2,2-DICHLORO-1,1-DIFLUORO-ETHOXY)PHENYL)SULFONYL)PROPANENITRILE

DESCRIPTION OF KNOWN PRIOR ART

S. A. Heininger, in U.S. Pat. No. 3,140,306, patented July 7, 1964, discloses 3-phenylsulfonyl-2-chloropropionitriles wherein the phenyl moiety may have halo substitution or lower alkyl substitution. These compounds are said to be microbiological toxicants. J. A. Stephens et al., in U.S. Pat. No. 3,140,226, patented July 7, 1964, disclose α-chloro-β-cyanoethylphenyl sulfones which may have halo or lower alkyl substitution on the phenyl moiety. The compounds, such as α-chloro-β-cyanoethylphenyl sulfone, are said to have bacteriostatic and fungistatic properties.

SUMMARY OF THE INVENTION

2-Chloro-3-((4-(2,2-dichloro-1,1-difluoroethoxy)-phenyl)sulfonyl)propanenitrile (hereinafter "Compound") is prepared by mixing together 4-(2,2-dichloro-1,1-difluoroethoxy)benzenesulfonyl chloride with substantially two molecular proportions of acrylonitrile in the presence of acetonitrile, cupric chloride and triethylamine hydrochloride whereby the following reaction takes place:

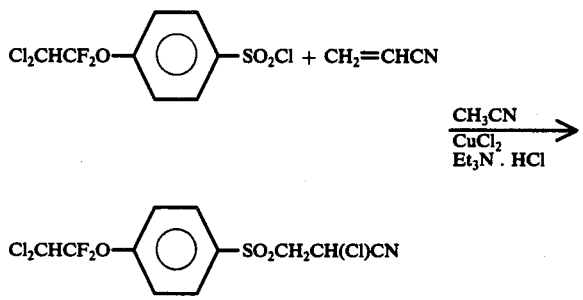

In the process, 4-(2,2-dichloro-1,1-difluoroethoxy)-benzenesulfonyl chloride (1 molar proportion), acrylonitrile (2 molar proportions), acetonitrile, anhydrous cupric chloride (.02 molar proportion) and triethylamine hydrochloride (0.032 molar proportion) are placed in a reaction vessel which is cooled, evacuated to about 2 mm mercury pressure, sealed and heated in an oil bath at about 115° C for about six hours. The vessel is opened and the product is isolated by crystallization from methanol to give the title compound as a white, crystalline solid, melting at 109° C.

DESCRIPTION OF SOME PREFERRED EMBODIMENTS

The following additional description and example further describe the invention and the manner and process of making and using it to enable the art skilled to make and use the same and set forth the best mode contemplated by the inventors of carrying out the invention.

The Compound has antimicrobial utility. When evaluated by the conventional in vitro agar Petri dish dilution test for determining bactericidal and fungicidal activity, the Compound gave 100 percent growth inhibition against the following organisms at the given concentrations in parts per million.

TABLE

| Organism | Minimum Inhibitory Concentration, ppm |
|---|---|
| P. aeruginosa | 50 |
| S. aureus | 5 |
| C. albicans | 50 |
| T. mentagrophytes | 50 |
| K. pneumoniae | 50 |
| P. chrysogenum | 50 |
| A. niger | 50 |
| B. subtilis | 1 |
| A. aerogenes | 50 |
| C. pelliculosa | 50 |
| P. pullulans | 50 |
| S. typhosa | 10 |
| Pseudomonas Sp. Strain 10 | 100 |
| C. ips | 50 |
| Trichoderm Sp. Madison P-42 | 100 |
| S. marcescens | 50 |
| Torulopsis Sp. | 50 |
| A. fumigatus | 50 |
| C. albicans | 50 |
| E. coli | 50 |

PREPARATION OF STARTING MATERIAL 4-(2,2-Dichloro-1,1-difluoroethoxy)benzenesulfonyl chloride is prepared in the following two-step process.

A. (2,2-Dichloro-1,1-difluoroethoxy)benzene

In a 500 ml stirred reaction flask equipped with thermometer, air condenser, dropping funnel and ice water bath was placed 94 g (one mole) of phenol and 300 ml of acetone and the mixture was cooled to 10° C. 11.0 Grams of powdered KOH (85 percent) was then added. After the mixture was stirred for one-half hour at 10° C, 2,2-dichloro-1,1-difluoroethene was introduced over period of one hour while maintaining the temperature at about 10–12° C. At the end of the addition of the dichlorodifluoroethene, a rapid reaction increased the temperature to 50° C. A Dry Ice$^{(R)}$ bath was substituted for the ice bath to cool the reaction mixture to 10° C. rapidly. After stirring overnight, the reaction mixture was poured over two liters of ice, stirred, allowed to settle and the oil layer was separated. The oil layer was washed with bicarbonate of soda solution and with water and the nearly colorless organic layer was separated. After drying over desiccant-grade magnesium sulfate, the organic layer was filtered to give the first-step product.

B. 4-(2,2-Dichloro-1,1-difluoroethoxy)benzenesulfonyl chloride

In a 500 ml stirred reaction flask equipped with thermometer, air condenser, dropping funnel and ice water bath was placed 60 ml of chlorosulfonic acid, and, while stirring at 0° to 10° C, there was added dropwise over a one-half hour period 0.1 mole of 2,2-dichloro-1,1-difluoroethoxybenzene. The reaction mixture was stirred for two hours while allowing the reaction temperature to reach room temperature. The reaction mixture was then poured over ice and both a viscous organic liquid and an aqueous liquid separated. The viscous liquid was separated from the aqueous layer and was dissolved in methylene chloride. The aqueous layer was also extracted with methylene chloride. Both methylene chloride solutions were dried over anhydrous magnesium sulfate, filtered, the solvent evaporated in vacuo to give the starting material as a light amber liquid. The following example describes a representative specific embodiment of the preparation of the compound of this invention.

EXAMPLE

2-Chloro-3-((4-(2,2-dichloro-1,1-difluoroethoxy)-phenyl)sulfonyl)propanenitrile In a 100 ml Fisher-Porter pressure vessel were placed 8.2 g (0.025 mole) of 4-(2,2-dichloro-1,1-difluoroethoxy)benzenesulfonyl chloride, 2.65 g (0.05 mole) of acrylonitrile, 2 ml of acetonitrile, 0.07 g (0.5 mmole) of anhydrous cupric chloride and 0.11 g (0.8 mmole) of triethylamine hydrochloride. After cooling and evacuating the vessel to 2 mm Hg pressure, it was sealed and heated in an oil bath at 115° C for 6 hours. The vessel was opened and the product isolated by crystallization from methanol to give 4.0 g of the title compound as a white, crystalline solid, mp 109° C.

Anal. Caculated for $C_{11}H_8Cl_3F_2NO_3S$: C, 35.23; H, 2.14; N, 3.72. Found: C, 35.16 H, 2.19; N, 3.89.

What is claimed is:
 1. 2-Chloro-3-((4-(2,2-dichloro-1,1-difluoroethoxy)-phenyl)sulfonyl)propanenitrile.

* * * * *